United States Patent [19]

Hartmann et al.

[11] 4,246,276
[45] Jan. 20, 1981

[54] COMBATING PESTS WITH 2,2-DIFLUORO-5-(2,4-DINITRO-6-TRI-FLUOROMETHYLPHENYLAMINO)-BENZODIOXOLES

[75] Inventors: Alfons Hartmann, Beckingen; Albrecht Marhold; Reinhard Lantzsch, both of Leverkusen; Ingeborg Hammann, Cologne; Paul-Ernst Frohberger, Leverkusen; Wilhelm Brandes, Leichlingen, all of Fed. Rep. of Germany

[73] Assignee: Bayer Aktiengesellschaft, Leverkusen, Fed. Rep. of Germany

[21] Appl. No.: 39,619

[22] Filed: May 16, 1979

[30] Foreign Application Priority Data

May 26, 1978 [DE] Fed. Rep. of Germany ....... 2823168

[51] Int. Cl.³ ............... A61K 31/36; C07D 317/44
[52] U.S. Cl. ............... 424/282; 260/340.5 R
[58] Field of Search ................ 260/340.5 R; 424/282

[56] References Cited

U.S. PATENT DOCUMENTS

| 3,683,008 | 8/1972 | Beregi et al. | 260/340.5 R X |
| 4,105,780 | 8/1978 | Barkelhammer et al. | 260/340.5 R X |
| 4,110,345 | 8/1978 | Berkelhammer et al. | 260/340.5 R X |

*Primary Examiner*—Ethel G. Love
*Attorney, Agent, or Firm*—Sprung, Felfe, Horn, Lynch & Kramer

[57] ABSTRACT

2,2-Difluoro-5-(2,4-dinitro-6-trifluoromethylphenylamino)-benzodioxoles of the formula

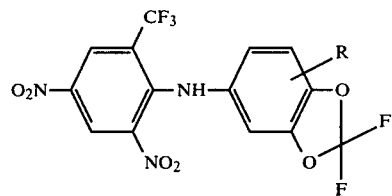

in which
R is hydrogen, halogen or alkyl optionally substituted by halogen, which possess arthropodicidal, microbicidal and herbicidal properties.

10 Claims, No Drawings

COMBATING PESTS WITH 2,2-DIFLUORO-5-(2,4-DINITRO-6-TRI-FLUOROMETHYLPHENYLAMINO)-BENZODIOXOLES

The present invention relates to and has for its objects the provision of particular new 2,2-difluoro-5-(2,4-dinitro-6-trifluoromethyl-phenylamino)-benzodioxoles which possess arthropodicidal, microbicidal and herbicidal properties, active compositions in the form of mixtures of such compounds with solid and liquid dispersible carrier vehicles, and methods for producing such compounds and for using such compounds in a new way especially for combating pests, e.g. insects, acarids, fungi and bacteria, with other and further objects becoming apparent from a study of the within specification and accompanying examples.

It is already known that certain diarylamines have insecticidal, acaricidal and fungicidal properties (see German Offenlegungsschrift (German Published Specification) 2,509,416. However, their action is not completely satisfactory, above all when low concentrations are applied.

The present invention now provides, as new compounds, the 5-arylamino-benzodioxoles of the general formula

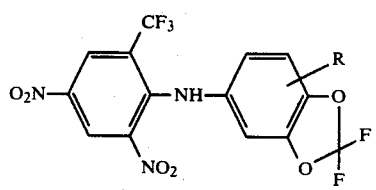

(I), in which
R represents hydrogen, halogen or alkyl which is optionally substituted by halogen.
Preferably R represents hydrogen, methyl or chlorine.

Surprisingly, the compounds of the formula (I) exhibit a considerably higher insecticidal, acaricidal and fungicidal potency than the substances known from Offenlegungsschrift (Published Specification) No. 2,509,416, which are chemically the most closely related substances of the same type of action. The compounds according to the invention thus represent a valuable enrichment of the art.

They display excellent insecticidal, acaricidal and fungicidal properties.

Preferably R represents hydrogen, methyl or chlorine.

The invention also provides a process for the preparation of a diarylamine of the formula (I) in which 2-chloro-3,5-dinitro-benzotrifluoride, of the formula

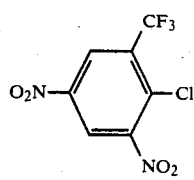

(II), is reacted with a 5-amino-benzodioxole of the general formula

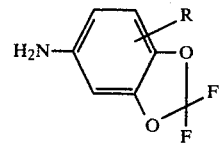

(III), in which
R has the meaning stated above, in the presence of an acid-binding agent and, if appropriate, in the presence of a diluent.

If 2-chloro-3,5-dinitro-benzotrifluoride and 5-amino-2,2-difluorobenzodioxole are used as starting substances, the course of the reaction can be represented by the equation which follows:

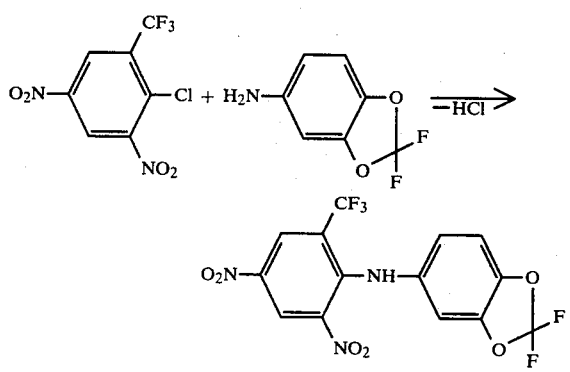

The compound 2-chloro-3,5-dinitro-benzotrifluoride to be used as a starting material is known. The compounds of the formula (III) also are known.

Of the compounds of the formula (II), 5-amino-2,2-difluoro-benzodioxole and 5-amino-6-chloro-2,2-difluoro-benzodioxole are particularly preferred.

Suitable diluents are inert organic solvents. Dimethylformamide or tetrahydrofuran are preferred. It is sometimes also advantageous to carry out the reaction in aqueous suspension.

Suitable acid-binding agents are bases, such as alkali metal hydroxides, carbonates or hydrides. Sodium bicarbonate potassium hydroxide or sodium hydride is preferably used.

The reaction temperature can be varied within a substantial range. In general, the reaction is carried out at from $-20°$ to $+150°$ C., preferably at from $0°$ to $100°$ C.

The reactants are usually employed in equimolar amounts.

As already mentioned, the compounds of the formula (I) have an insecticidal, acaricidal and fungicidal action. When relatively high concentrations are applied, some compounds of the formula (I) also have a herbicidal action.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

Bactericidal agents are employed in plant protection for combating Pseudomonadaceae, Rhizobiaceae, Enterobacteriaceae, Corynebacteriaceae and Streptomycetaceae.

The good toleration, by plants, of the active compounds, at the concentrations required for combating plant diseases, permits treatment of above-ground parts of plants, of vegetative propagation stock and seeds, and of the soil.

The active compounds are well tolerated by plants, have a favorable level of toxicity to warm-blooded animals, and can be used for combating arthropod pests, especially insects and acarids, which are encountered in agriculture, in forestry, in the protection of stored products and of materials, and in the hygiene field. They are active against normally sensitive and resistant species and against all or some stages of development. The abovementioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and *Scutigera spec.;* from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana, Heliothis spp., Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus,* Oscinella frit, Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp..

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alchols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol esters, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

In the veterinary field, the active compounds according to the invention may be used in a known manner, such as orally in the form of, for example, tablets, capsules, drenches and granules; dermally by means of, for example, dipping, spraying, pouring-on, spotting-on and powdering; and parenterally, for example by means of injections.

In the treatment of seed, amounts of active compound of 0.001 to 50 g, especially 0.05 to 5 g, are generally employed per kilogram of seed.

For the treatment of soil, amounts of active compound of 0.00001 to 0.1% by weight, especially 0.0001 to 0.02%, are generally employed at the place of action.

The present invention also provides an arthropodicidal or microbicidal composition containing as active ingredient a compound of the present invention in admixture with a solid or liquefied gaseous diluent or carrier or in admixture with a liquid diluent or carrier containing a surface-active agent.

The present invention also provides a method of combating arthropods (especially insects or acarids) or micro-organisms (especially fungi) which comprises applying to the arthropods or micro-organisms, or to a habitat thereof, a compound of the present invention alone or in the form of a composition containing as active ingredient a compound of the present invention in admixture with a diluent or carrier.

The present invention also provides a method of freeing or protecting domesticated animals from parasitical insects or acarids which comprises applying to said animals a compound according to the present invention, in admixture with a diluent or carrier.

The present invention further provides crops protected from damage by arthropods or microbes by being grown in areas in which immediately prior to and/or during the time of the growing a compound of the present invention was applied alone or in admixture with a diluent or carrier.

It will be seen that the usual methods of providing a harvested crop may be improved by the present invention.

The present invention further provides domesticated animals whenever freed or protected from parasitical insects or acarids by the application of said animals of a compound according to the present invention, in admixture with a diluent or carrier.

Preparation of the novel compounds is shown in the following illustrative examples:

EXAMPLE 1

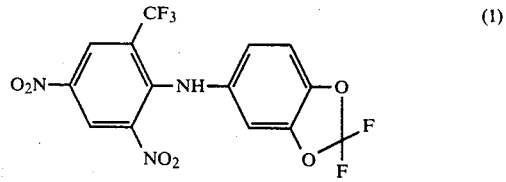

19.0 g (0.07 mol) of 2-chloro-3,5-dinitro-benzotrifluoride and 12.1 g (0.07 mol) of 5-amino-2,2-difluorobenzodioxole were suspended in 100 ml of water. 6 g of sodium bicarbonate were added and the mixture was heated under reflux for 2 hours. After cooling, the precipitate was filtered off and washed with water and methanol, whereupon 16.3 g of yellow crystals of melting point 122° C. were obtained.

EXAMPLE 2

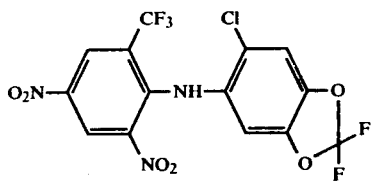

A solution of 13.5 g (0.05 mol) of 2-chloro-3,5-dinitro-benzotrifluoride in 100 ml of dimethylformamide was added dropwise to 10.4 g (0.05 mol) of 5-amino-6-chloro-2,2-difluoro-benzodioxole and 5.6 g (0.1 mol) of potassium hydroxide powder in 100 ml of dimethylformamide at 20° C., while stirring. The mixture was stirred at room temperature for 15 hours, 50 ml of glacial acetic acid were added and the mixture was poured onto ice, whereupon 6-chloro-2,2-difluoro-5-(2,4-dinitro-6-trifluoromethylphenylamino)-benzodioxole separated out as a dark, viscous oil. Molecular weight 441, Cl₁ (according to mass spectroscopy).

The insecticidal, acaricidal and fungicidal activity of the compounds of this invention is illustrated by the following biotest examples wherein the compounds according to the present invention are each identified by the number (given in brackets) from the preparative examples hereinabove:

EXAMPLE 3

Tetranychus test (resistant)
Solvent: 3 parts by weight of dimethylformamide
Emulsifier: 1 part by weight of alkylaryl polyglycol ether To produce a suitable preparation of active compound, 1 part by weight of the active compound was mixed with the state amount of solvent and the stated amount of emulsifier and the concentrate was diluted with water to the desired concentration.

Bean plants (*Phaseolus vulgaris*) which were heavily infested with the two-spotted spider mite (*Tetranychus urticae*) in all stages of development were treated by being dipped into the preparation of the active compound of the desired concentration.

After the specified periods of time, the degree of destruction was determined. In this test compounds (1) and (2) showed a superior activity compared to the prior art.

EXAMPLE 4

Myzus test (contact action)
Solent: 3 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were treated by being dipped into the preparation of active compound of the desired concentration.

After the specified periods of time, the degree of destruction was determined. In this test compounds (1) and (2) showed a superior activity compared to the prior art.

EXAMPLE 5

Podosphaera test (apple)/protective
Solvent: 4.7 parts by weight of acetone
Emulsifier: 0.3 part by weight of alkylaryl polyglycol ether
Water: 95 parts by weight The amount of active compound required for the desired concentration of the active compound in the spray liquid was mixed with the stated amount of solvent, and the concentrate was diluted with the stated amount of water which contained the stated amount of emulsifier.

Young applie seedlings in the 4-6 leaf stage were sprayed with the spray liquid until dripping wet. The plants remained in a greenhouse for 24 hours at 20° C. and at a relative atmospheric humidity of 70%. They were then inoculated by dusting the conidia of the apple powdery mildew causative organism (*Podosphaera leucotricha*) and placed in a greenhouse at a temperature of 21°-23° C. and at a relative atmospheric humidity of about 70%.

10 days after the inoculation, the infection of the seedlings was determined. In this test compounds (1) and (2) showed a superior activity compared to the prior art.

EXAMPLE 6

Fusicladium test (apple)/protective
Solvent: 4.7 parts by weight of acetone
Emulsifier: 0.3 part by weight of alkylaryl polyglycol ether
Water: 95 parts by weight The amount of active compound required for the desired concentration of the active compound in the spray liquid was mixed with the stated amount of solvent, and the concentrate was diluted with the stated amount of water which contained the stated amount of emulsifier.

Young applie seedlings in the 4-6 leaf stage were sprayed with the spray liquid until dripping wet. The plants remained in a greenhouse for 24 hours at 20° C. and at a relative atmospheric humidity of 70%. They were then inoculated with an aqueous conidium suspension of the applie scab causative organism (*Fusicladium dendriticum*) and incubated for 18 hours in a humidity chamber at 18°-20° C. and at a relative atmospheric humidity of 100%.

The plants were then brought into a greenhouse again for 14 days.

15 days after inoculation, the infection of the seedlings was determined. In this test compounds (1) and (2) showed a superior activity compared to the prior art.

EXAMPLE 7

Shoot treatment test/cereal rust
(leaf-destructive mycosis)/protective

To produce a suiable preparation of active compound, 0.25 part by weight of active compound was taken up in 25 parts by weight of dimethylformamide and 0.06 part by weight of alkylaryl polyglycol ether and then 975 parts by weight of water were added. The concentrate was diluted with water to the desired final concentration of the spray liquor.

To test the protective activity, one-leaved young wheat plants of the Michigan Amber variety were inoculated with a uredospore suspension of *Puccinia recondita* in 0.1% strength aqueous agar. After the spore suspension had dried on, the wheat plants were sprayed with the preparation of active compound until dew-moist and were placed, for incubation, in a greenhouse for 24 hours at about 20° C. and 100% relative atmospheric humidity.

After 10 days' dwell time of the plants at a temperature of 20° C. and 80–90% atmospheric humidity, the occurrence of rust pustules on the plant was evaluated.

The more active the compound, the lower was the degree of rust infection.

In this test compounds (1) and (2) exhibited a superior activity compared to the prior art.

EXAMPLE 8

Shoot treatment test/powder mildew of cereals/protective

To produce a suitable preparation of active compound, 0.25 part by weight of active compound was taken up in 25 parts by weight of dimethylformamide and 0.06 part by weight of alkyllaryl polyglycol ether; 975 parts by weight of water were then added. The concentrate was diluted with water to the desired final concentration of the spray liquor.

To test for protective activity, single-leaved young barley plants of the Amsel variety were sprayed with the preparation of active compound until dew-moist. After drying, the barley plants were dusted with spores of *Erysiphe graminis* var. hordei.

After 6 days' dwell time of the plants at a temperature of 21°–22° C. and 80–90% atmospheric humidity the occurrence of mildew pustules on the plants was evaluated. The more active the compound, the lower was the degree of mildew infection.

In this test compounds (1) and (2) showed a superior activity compared to the prior art.

It will be appreciated that the instant specification and examples are set forth by way of illustration and not limitation, and that various modifications and changes may be made without departing from the spirit and scope of the present invention.

What is claimed is:

1. A 2,2-difluoro-5-(2,4-dinitro-6-trifluoromethyl-phenylamino)-benzodioxole of the formula

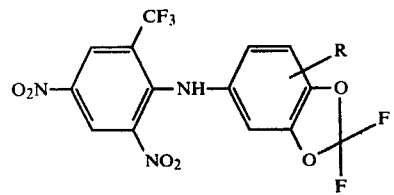

in which
R is hydrogen, halogen or alkyl optionally substituted by halogen.

2. A compound according to claim 1, in which R is hydrogen, methyl or chlorine.

3. A compound according to claim 1, wherein such compound is 2,2-difluoro-5-(2,4-dinitro-6-trifluoromethylphenylamino)-benzodioxole of the formula

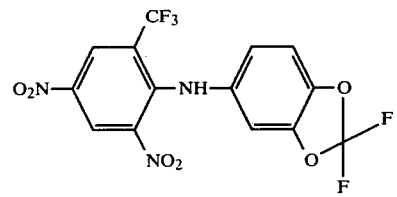

4. A compound according to claim 1, wherein such compound is 6-chloro-2,2-difluoro-5-(2,4-dinitro-6-trifluoromethyl-phenylamino)-benzodioxole of the formula

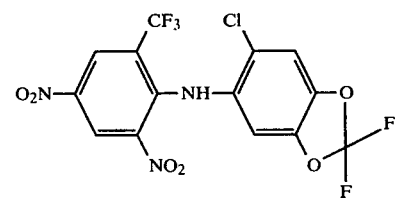

5. An arthropodicidal or microbicidal composition containing as active ingredient on arthropodicidally or microbicidally effective amount of a compound according to claim 1 in admixture with a diluent.

6. A composition according to claim 5, wherein such compound is 2,2-difluoro-5-(2,4-dinitro-6-trifluoromethylphenylamino)-benzodioxole.

7. A composition according to claim 5, wherein such compound is 6-chloro-2,2-difluoro-5-(2,4-dinitro-6-trifluoromethyl-phenylamino)-benzodioxole.

8. A method of combating arthropods or microbes which comprises applying to the arthropods or microbeds, or to a habitat thereof, an arthropodicidally or microbicidally effective amount of a compound according to claim 1.

9. The method according to claim 8, wherein such compound is 2,2-difluoro-5-(2,4-dinitro-6-trifluoromethylphenylamino)-benzodioxole.

10. The method according to claim 8, wherein such compound is 6-chloro-2,2-difluoro-5-(2,4-dinitro-6-trifluoromethyl-phenylamino)-benzodioxole.

* * * * *

UNITED STATES PATENT AND TRADEMARK OFFICE
CERTIFICATE OF CORRECTION

PATENT NO. : 4,246,276
DATED : Jan. 20, 1981
INVENTOR(S) : Alfons Hartmann et al It is certified that error appears in the above—identified patent and that said Letters Patent is hereby corrected as shown below:

Column 10, Line 34  Delete "on" and insert --an--.

Column 10, Line 44-45  Delete "microbeds" and insert --microbes--.

Signed and Sealed this

Ninth Day of June 1981

[SEAL]

Attest:

RENE D. TEGTMEYER

Attesting Officer     Acting Commissioner of Patents and Trademarks